Aug. 7, 1934. J. C. GANO Plant Pat. 100
AVOCADO
Filed Nov. 23, 1932
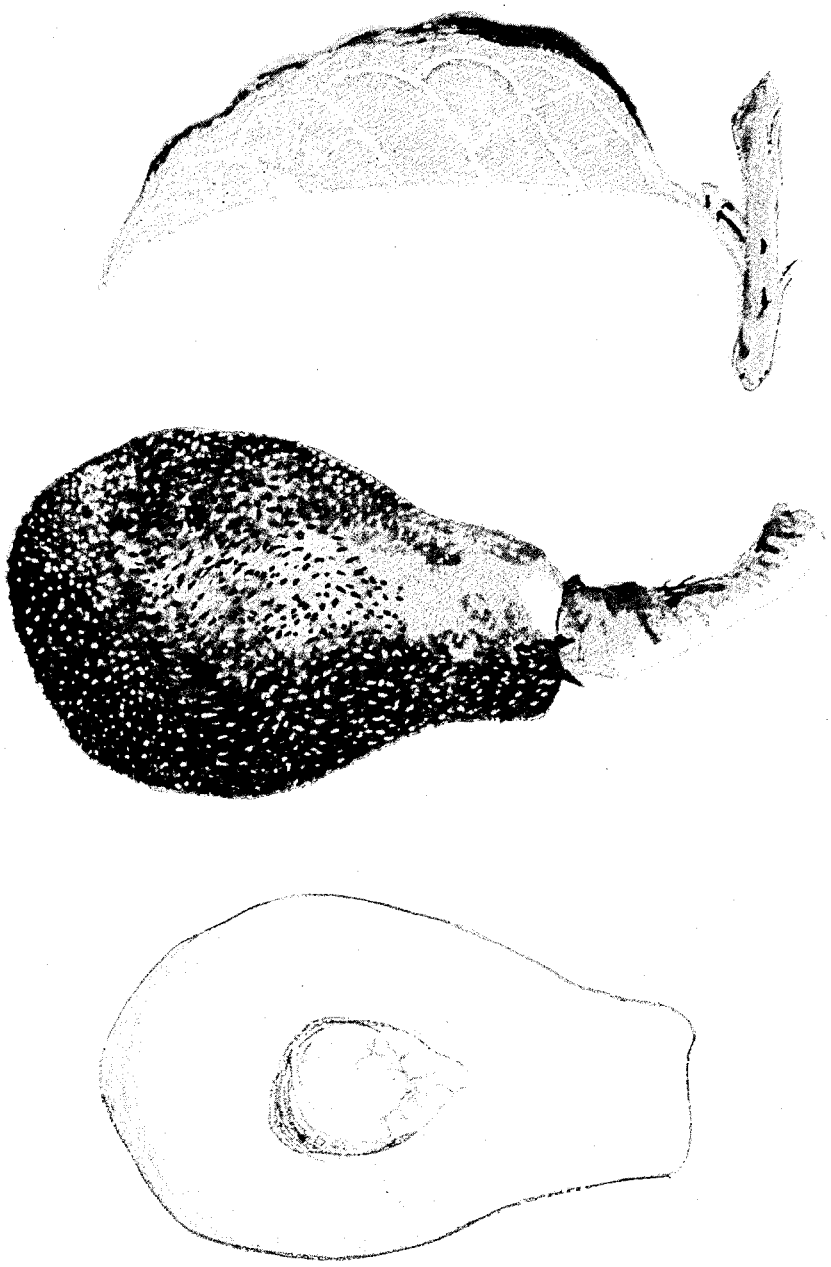
Inventor
Jennie C. Gano
By- Lyon & Lyon
Attorneys Patented Aug. 7, 1934

Plant Pat. 100

UNITED STATES PATENT OFFICE

100

AVOCADO

Jennie C. Gano, Whittier, Calif.

Application November 23, 1932, Serial No. 644,015

1 Claim. (Cl. 47—62)

This invention relates to a new and distinct variety of avocado having certain highly desirable characteristics as will appear hereinafter. Although the parentage of this tree is not known, it is believed to have originated as a chance seedling of Colorado variety.

The new and distinct variety of avocado embraced by this invention matures during the summer months, namely, during the months of July and August. These months of maturity apply particularly to this variety of avocado when raised at or about the town of Whittier, California.

Avocados which normally mature during the summer months belong to the Sharples, Benick and Murrieta Green varieties. The Sharples and Benick avocados are purple in color whereas the Murrieta Green is a very dark green, round fruit. The fruit of the avocado of this invention may be readily distinguished from the other summer varieties as it is pyriform in shape, the fruit becoming longer as it matures. In general, it may be said that the fruit of this invention resembles the Fuerte in appearance but the Fuerte matures during the winter months only.

The young fruit produced by the trees of this invention are glossy dark green in color. If the fruit is picked while still green, it has a tendency to turn purple in color. As the fruit matures, it loses its glossy appearance, the background becoming a dull yellowish green in color, similar to the shade shown on Plate XXXII—31—*m* in Ridgway's Color Dictionary. This background shows spots of a color shown on Plate V—25—*f* and *d*. Brown pimples form over the surface of the fruit at maturity (Plate XV—17—*m*). The skin of the mature fruit of this invention is slightly thicker than that of the Fuerte (measuring about 0.05 centimeters) but not as thick as the skin on Colorado fruits. Young trees bear fruit varying in size from about 14 to 20 ounces. As the tree gets older and bears heavier crops, the average size of the fruit decreases to between 12 and 14 ounces. The fruit may vary from 13 to 17 centimeters in length, having a maximum width of from 8.5 to 10.5 centimeters. A 17½ ounce fruit measured 5½ inches in length and had a maximum width of 3⅜ inches.

The seed is similar in size to that of the Fuerte and is in the same relative position in the fruit but is slightly more pointed. A 14 ounce fruit, for example, has a seed weighing about 2 ounces. The seeds are generally tight in the cavity of the fruit and are provided with a brown covering. Although the majority of avocado seeds have a tendency to split into two lobes, the seeds found in fruit borne by the tree of this invention have three lobes.

The flesh of the fruit of this invention is a light yellow in color, being lighter in this respect than the Fuerte fruit. The flesh is firm and is substantially free from fiber. It has a highly desirable oil content. The flesh close to the skin has a color similar to that shown in Plate VI—31—yellow green, while that close to the seed is similar to the shade shown in Plate V—25—YGY—*f*.

It has been found that the new variety is most successfully propagated in southern California by budding on Ganter seedlings as root stock. The trees are very prolific and exhibit a well balanced branch system. In general habit, the trees are vigorous, upright, and tending to be slender in the younger trees. The lower branches droop somewhat but those farther up the tree extend substantially horizontally and appear to be equally spaced around the tree. The young branches of the tree are olive green in color with dark green, relatively long and profuse lenticels on the upper surfaces of the branches. The lower surfaces of the branches have small and substantially round lenticels. The young branches are of substantially the same color as those of the Fuerte but the lenticels of the Fuerte are not as profuse nor as long nor as distinct. The lenticels of the young branch wood of the Colorado variety are relatively scarce in comparison with the number found on similar young branch wood of the tree of this invention.

One of the most distinctive characteristics of the tree of this invention is the foliage. The new growth presents a rather bunched appearance about the terminal, the newly formed leaves being broader in shape at the base than in the Fuerte. The veining is pronounced and in very freshly formed leaves tends to give the leaf surface a somewhat puckered appearance. The young leaves which occur during the summer months are of a bronze or reddish brown color (containing more gold tones than the shade shown in Plate XV—15—*k*). The young leaves of the Pueblo variety are light green, whereas the young leaves of the Fuerte resemble those found on the present tree. During the winter months the young leaves which occur on the tree of this invention are green in color and similar to those of the Pueblo but quite distinct from those of the Fuerte variety.

The mature leaves of the tree of this invention are longer and of a darker green than the leaves of the Pueblo variety. The top surface of the mature leaves is similar in color to the shade shown on Plate XLI—29—*m*. The lower surface of these leaves resembles the shade shown on Plate XLI—29—*i*. The mature growth is closely set and protective to the limbs of the tree. The mature leaves are long, lanceolate in shape, with a pronouncedly rippled edge. The mature leaves of the Fuerte, on the other hand, are slightly lighter in color and appreciably shorter and broader. The mature leaves may vary in length from about 13 to 18 centimeters, with a maximum width of from about 5.5 to 6.2 centimeters. The mature leaves of the tree of this invention are curly at the edges, the undulations being much more pronounced than those of the Pueblo leaves. Although the upper surface of the leaf is smooth, the lower surface is dull, the veins protruding appreciably and exhibiting a relatively high proportion of branching veins which interconnect.

A further distinguishing characteristic of the tree of this invention is the profuse and peculiar bud wood capable of being used for propagation. The Guatemalan varieties of avocado have buds which are generally referred to as rosebuds, having four outwardly curling petals or bud scales. The buds on the Pueblo and Fuerte trees have no visible bud scales at all but instead are apparently solid and pointed. The buds on the tree of this invention, however, are relatively large and have two opposing, outwardly curving petals or bud scales. Three to four times as many buds may be found on a branch of the avocado of this invention as appear on a similar branch of either the Pueblo or Fuerte variety. Not only is the bud wood profuse but in addition it is very easy to bud trees therewith.

In blossoming characteristics the avocado of this invention is similar to the Guatemalan varieties, such as the Murrieta Green and Colorado. The bloom grows in small bunches distributed along the limbs and blooming does not cause the leaves to be shed as completely as is the case with the Fuerte variety. It may be stated that the avocado tree of this invention exhibits axillary flowering characteristics where as most other varieties exhibit terminal flowering characteristics. As a result, the fruit is set so far back of the terminals that it is more thoroughly covered then is usually the case in other varieties.

The avocado trees of this invention are capable of bearing fruit when only twenty-four months old. The Fuerte variety, on the other hand, will not bear until three or four years old. The fruit hangs well, depending from relatively short yellow stems tinged with green, the stems being of appreciably larger diameter than those found on the Fuerte. For example, the stems will be about 0.8 to 1.1 centimeters in diameter and have a length of from about 5 to 7 centimeters. The color of the stems may vary between the shades shown on Plates V—27—*b* and V—25—*d*. The button is unusually large, being of appreciably larger diameter than the stem (measuring from about 1.2 to 1.5 centimeters) but being relatively short in proportion to its diameter. A distinct line of demarcation between the button and the stem of the fruit exists. The button does not leave a cavity of any appreciable size in the fruit.

It is to be understood that although the description given herein above accurately represents and describes the tree, foliage and fruit, the general characteristics may vary slightly due to climatic conditions, soil, etc.

The distinguishing characteristics of the tree of this invention appear to be the time of maturity, the propagating bud provided with two bud scales, the curly leaf and the relatively thick stem and button.

I claim:

An avocado tree substantially as described, bearing a green colored pear-shaped fruit ripening during the summer months.

JENNIE C. GANO.